(12) United States Patent
Nishino et al.

(10) Patent No.: US 6,465,236 B1
(45) Date of Patent: Oct. 15, 2002

(54) THERMOSTABLE COLLAGEN-DIGESTING ENZYME, NOVEL MICROORGANISM PRODUCING THE ENZYME AND PROCESS FOR PRODUCING THE ENZYME

(75) Inventors: Tokuzo Nishino; Toru Nakayama; Naoki Tsuruoka; Minoru Akai, all of Sendai (JP)

(73) Assignee: Japan Science and Technology Corporation, Saitama-ken (JP)

( * ) Notice: Subject to any disclaimer, the term of this patent is extended or adjusted under 35 U.S.C. 154(b) by 0 days.

(21) Appl. No.: 09/807,745

(22) PCT Filed: Nov. 16, 1999

(86) PCT No.: PCT/JP99/06392

§ 371 (c)(1),
(2), (4) Date: Apr. 18, 2001

(87) PCT Pub. No.: WO01/16302

PCT Pub. Date: Mar. 8, 2001

(30) Foreign Application Priority Data

Aug. 30, 1999 (JP) ............................................. 11-242816

(51) Int. Cl.$^7$ ............................. C12N 9/54; C12N 1/20; C12N 9/52
(52) U.S. Cl. ................. 435/221; 435/252.5; 435/252.1; 435/219; 435/220
(58) Field of Search ............................. 435/221, 252.5, 435/252.1, 219, 220

(56) References Cited

U.S. PATENT DOCUMENTS 4,315,988 A    2/1982   Miwa et al. ................ 435/221

OTHER PUBLICATIONS

Sako et al. An extremely heat–stable extracellular proteinase (aeropyrolysin) from the hyperthermophilic archaeon aeropyrum pernix K1 Febs Letters 415:329–334 1997.

Asdornnithee S. et al., "Isolation and Characterization of a Collagenolytic . . .", Journal of Fermentation and Bioengineering, 1994, vol. 78, No. 4, pp. 283–287.

Kawahara H. et al., Isolation and Characterization of New Type of Colagenase . . . Biosci. Biochem., 1993, vol. 57, No. 8, pp. 1372–1373.

Makinen K.K. et al., "Purification and Properties of an Extracellular . . .", J. Biol. Chem., 1987, vol. 262, No. 26, pp. 12488–12495.

Kabadjova P. et al., "Isolation and Distribution of Streptomyces . . . ", Folia Microbila., 1996, vol. 41, No. 5, pp. 423–429.

*Primary Examiner*—Rebecca E. Prouty
*Assistant Examiner*—Delia Ramirez
(74) *Attorney, Agent, or Firm*—Sherman & Shalloway

(57) ABSTRACT

Bacillus sp. NTAP-1 having been deposited under accession number FERM BP-6926; and a collagen-decomposing enzyme produced by bacterium. The above enzyme (1) has a capability of hydrolyzing, at the highest efficiency, collagen and gelatin from among casein, gelatin, albumin and collagen; (2) shows the optimum pH of 3.5 to 4.5; (3) shows the optimum temperature of 65 to 70° C.; (4) after heating at 60° C. at pH 6.0 for 4 hours, sustains an activity amounting to 60% or more of the level before the heat treatment; (5) remains stable at pH 3 to 6; and a molecular weight of approximately 46,000 when measured by SDS-PAGE.

4 Claims, 4 Drawing Sheets

THERMOSTABLE COLLAGEN-DIGESTING ENZYME, NOVEL MICROORGANISM PRODUCING THE ENZYME AND PROCESS FOR PRODUCING THE ENZYME

FIELD OF THE INVENTION

The present invention relates to a thermostable collagen-decomposing enzyme produced by a new microorganism, and said new microorganism and a method for production of said enzyme by said microorganism. Concretely, the present invention relates to a novel thermostable collagen-decomposing enzyme having the highest reactivity (substrate specificity) to collagen, produced by a novel microorganism of the genus Bacillus, said novel microorganism and a process for producing of said enzyme by said microorganism.

DESCRIPTION OF THE PRIOR ART

Collagen-decomposing and gelatin-decomposing enzymes have been widely used in industry. For example, collagen peptides, which are hydrolytic products from collagen by these enzymes, are useful as material for cosmetics, because of their interesting physiological activities such as moisture-keeping effects or immunity-activation activity. Therefore, collagen peptides are widely used for medical and cosmetic purposes. Further, gelatin, which is a denaturated form of collagen, is used as the coating material for photograph films, and gelatin-decomposing enzymes are used for the recycling of the photograph and X-ray films. Many kinds of proteases are known to decompose difficult. For hydrolysis of collagen, specific metal proteases, named "collagenase", should be used.

Recently, many attempts have been made for the effective use of the organic wastes. For instance, the composing of garbage wastes is one concrete example of the biorecycling of organic wastes. More than 30% of animal protein are composed of collagen, therefore, garbage wastes produced from daily kitchen activities in houses and restaurants and the wastes from meat processing factories should contain large quantities of collagen.

Because of specific, highly ordered structure, collagen is generally insoluble in water and difficult to be decomposed, and therefore degradation of collagen proceeds very slowly during composing. Most part of unusable portions produced from livestock industries are composed of collagen, and, therefore, are treated by incineration, causing problems such as anathermal of the earth or the generation of carbon dioxide or dioxin which cause the air pollution.

These problems must be solved from the view point to make an effective use of materials.

It is well known that the temperature of the organic wastes raises to 50–65° C. or higher during the composing process. Therefore, if thermostable enzymes or thermophilic microorganisms which are active even under such high-temperature composing conditions are used, the composing of organic waste should proceed more effectively.

Nowadays, industrial collagenases are those from microorganisms (bacteria), and as a concrete example, an actinomycetous collagenase of the genus Streptomyces can be mentioned. Other microbial collagenases are also known; for instance, collagenases from Clostridium hystolyticum (Biochemistry 1984, 23, 3077–3085) and Cytophaga sp. (Biosci, Biotech, Biochem., 1993, 57, 1894–1898) are the concrete examples.

Concerning the example of enzyme which is industrially used, it is necessary for the enzyme to be thermostable from the view point of treating speed and the subject to be treated. However, all known collagenases are of mesophilic origin and lacks of thermostability, and these circumstances hampers their efficient industrial applications. Until now, a collagen-decomposing enzyme with sufficient thermostability (having high optimum temperature) for the industrial applications has not yet been developed.

Usually, it is difficult to use collagen in an industrial scale because there is no thermostable enzyme to act effectively in an industrial scale. Therefore, it is obvious that above mentioned problem can be solved perfectly, if an enzyme having high activity to collagen is developed.

As mentioned above, the object of this invention is to find out a thermostable collagen-decomposing enzyme.

The inventors of this invention have carried out an intensive study to find a microorganism producing a thermostable collagen-decomposing enzyme in nature, and have found a promising thermophilic bacterium belonging to the genus Bacillus genus that produces said enzyme in the soil of Sendai, Japan and accomplished the present invention.

The microorganism, which is used to produce a thermostable collagen-decomposing enzyme of this invention, belongs to the genus Bacillus, and is termed strain NTAP-1. This strain has been deposited according to the requirement of deposit based on Budapest treaty in the Biotic Technology Industries Institute of the Agency of Industrial Science of Technology belonging to the Ministry of International Trade and Industry Japan and accepted by the accept number of FERM BP-6926 on Nov. 1, 1999 Biotic Technology Industries Institute, Agency of Industrial Science and Technology 1-3, Higashi 1-chome Tsukuba-shi, Ibaraki-ken 305-0046 JAPAN. (This strain is originally deposited on Aug. 27, 1999 under accession number FERM P-17535.) (in the specification, this strain is shortened only as <NTAP-1 strain>)

The inventors of this invention have found out that the industrially useful enzyme can be obtained by the use of this strain, and the obtained enzyme can be used as the catalyst for bioconversion.

DETAILED DESCRIPTION OF THE INVENTION

The first important point of this invention is a thermostable collagen-decomposing enzyme obtained by the microorganism having a thermostable collagen-decomposing activity and belonging to the genus Bacillus, which is characterized by the following features; (1) the bacterium is Gram-negative or Gram-indefinite, (2) the bacterium has a spore forming ability, (3) the bacterium is motile, (4) the bacterium grows at 70° C., does not grow at 30° C. or 80° C. and grows at pH 5, does not grow at pH 7, (6) the bacterium is rod-shaped, (7) the bacterium is negative to catalase, (8) the bacterium is negative to oxidase, (9) the bacterium is negative to O/F test, (10) the bacterium has acetoin producing activity and (11) the bacterium has gelatin decomposition activity. Accordingly, an excellent action and effect which can be used for the decomposition of collagen at 70° C. or lower temperatures can be expected.

Desirably, said thermostable collagen-decomposing enzyme of this invention is characterized by the following features: (1) the enzyme can far more effectively hydrolyze collagen and gelatin than casein and albumin, (2) optimum reaction pH is between pH 3.5 and 4.5, (3) optimum reaction temperature is between 65° C. and 70° C., (4) the enzyme retains more than 60% of its original activity after heat treatment at 60° C. and pH 6.0 for 4 hours, (5) the enzyme is stable between pH 3 to 6 and (6) molecular weight of the enzyme estimated by SDS-polyacrylamide gel electrophoresis is approximately 46,000. And more desirably, said thermostable collagen-decomposing enzyme of this invention is produced by the microorganism belonging to the genus Bacillus or Bacillus sp. strain NTAP-1.

The second important point of this invention is a producing method of the thermostable collagen-decomposing enzyme comprising, using a microorganism which has following features, that is, by the following features: (1) the bacterium is Gram-negative or Gram-indefinite, (2) the bacterium has a spore forming ability, (3) the bacterium is motile, (4) the bacterium grows at 70° C., does not grow at 30° C. or 80° C. and grows at pH 5, does not grow at pH 7, (6) the bacterium is rod-shaped, (7) the bacterium is negative to catalase, (8) the bacterium is negative to oxidase, (9) the bacterium is negative to O/F test, (10) the bacterium has acetoin producing activity and (11) the bacterium has gelatin decomposition activity, purifying and accumulating the thermostable collagen-decomposing enzyme which has following features: (1) the enzyme can far more effectively hydrolyze collagen and gelatin than casein and albumin, (2) optimum reaction pH is between pH 3.5 and 4.5, (3) optimum reaction temperature is between 65° C. and 70° C., (4) the enzyme retains more than 60% of its original activity after heat treatment at 60° C. and pH 6.0 for 4 hours, (5) the enzyme is stable between pH 3 to 6 and (6) molecular weight of the enzyme estimated by SDS-polyacrylamide gel electrophoresis is approximately 46,000, in a culture medium and by collecting it.

Desirably, the producing method of said thermostable collagen-decomposing enzyme, wherein the microorganism belonging to the genus Bacillus is the Bacillus genus bacteria NTAP-1 strain.

The third important point of this invention is a new developed microorganism belonging to a Bacillus genus, which produces said thermostable collagen-decomposing enzyme, desirably, said microorganism is the strain titled as Bacillus sp. NTAP-1 and have deposited according to the requirement of deposit based on Budapest treaty in the Biotic Technology Industries Institute of the Agency of Industrial Science of Technology belonging to the Ministry of Intentional Trade and Industry Japan and accepted by the accession number FERM BP-6926 on Nov. 1, 1999 Biotic Technology Industries Institute, Agency of Industrial Science and Technology 1-3, Higashi 1-chome Tsukuba-shi, Ibaraki-ken 305-0046 JAPAN. (This strain is originally deposited on Aug. 27, 1999 under accession number FERM P-17535.).

The inventors of this invention have found that among the microorganism belonging to Bacillus genus there is a novel microorganism which produces thermostable collagen-decomposing enzyme, and have accomplished the present invention.

BRIEF ILLUSTRATION OF THE DRAWINGS

FIG. 1 is a graph showing the heat stability of the thermostable collagen-decomposing enzyme, FIG. 2 is a graph showing the pH-stability of said thermostable collagen-decomposing enzyme, FIG. 3 is a graph showing the temperature-dependence of the reaction of said thermostable collagen-decomposing enzyme and FIG. 4 is a graph showing the pH-dependence of the reaction of said thermostable collagen-decomposing enzyme.

THE BEST EMBODIMENT OF THE INVENTION

The present invention will be illustrated more in detail.
A. The Microbiological Features of Bacteria used to Produce a Thermostable Collagen-decomposing Enzyme are Mentioned above. Further, this Microorganism can be Preserved by Freezing Method (−80° C. around).
B. Growing Condition
   name of cultivate medium: GGY medium
   components of medium: medium containing 1.5% of glucose, 1.5% of gelatin and 0.01% of yeast extract.
   pH of medium: 4.8
   sterilizing condition of medium: 20 minutes at 120° C.
   temperature of medium: 60° C.
   aerobic condition
C. Component of Protecting Agent: 30% Glycerol Aqueous Solution (not Necessary to Adjust pH of Protecting Agent)
   not necessary to adjust pH of protecting agent
   sterilizing condition of protecting agent: 20 minutes at 120° C.

The characteristics of the thermostable collagen-decomposing enzyme of this invention will be illustrated more minutely with reference to the drawings.

EXAMPLES

Example 1

Figure 1:
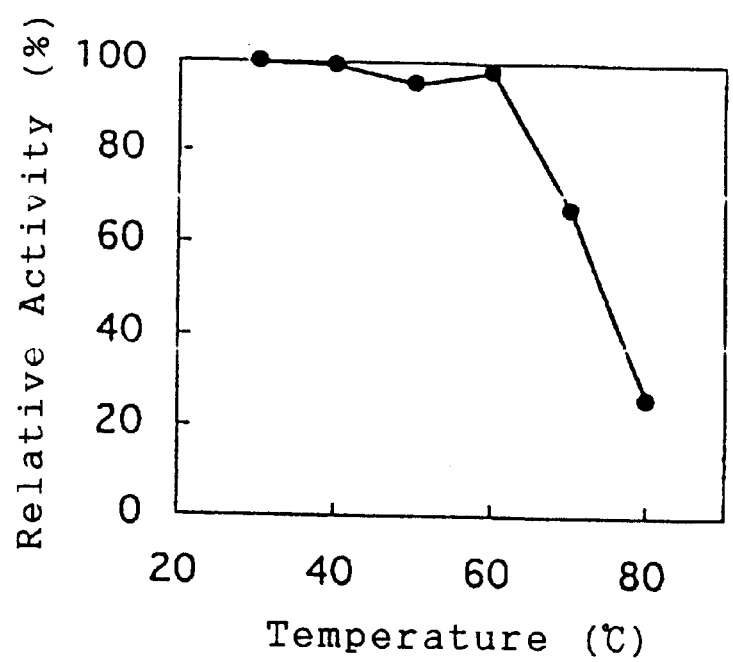
FIG. 1 is the graph showing the relative remaining activity of the thermostable collagen-decomposing enzyme after heat treatment at various temperature for 1 hour, and in this graph, the activity after heat treatment at 30° C. is taken to be 100%.

Various kinds of specimen such as soils, composts, river and lake waters are diluted to 100–10,000 times with 0.85% NaCl, and 0.1 ml of said diluted solution was spread on GGY agar-agar medium, then are left for 2 or 3 days at 70° C. The colony grown on medium was isolated and inoculated in 5 ml of GGY liquid medium and cultivated with shaking for 2 or 3 days at 70° C. The collagen-decomposing enzyme activity of several hundred kinds of isolates are evaluated using the supernatant of culture according to the method described in Example 2.

The strain that indicates the highest collagen-decomposing activity was selected and named it NTAP-1 strain.

The taxonomical characteristics of NTAP-1 strain can be illustrated as follows.
(1) cell morphology: rod-shaped (0.8×2–3 μm), curved and becomes chain form by aging.
(2) Gram's staining: negative or indefinite
(3) spore forming ability: yes
(5) motility: yes
(5) shape and characteristic of colonies: circular, corrugated or slightly convex, having smooth surface and transparent.
(6) growing temperature: grows at 70° C., but does not grow at 80° C.

(7) catalase: negative
(8) oxidase: negative
(9) O/F test: negative
(10) biochemical test:

Decomposes glucose, fructose, sorbose, D-arabinose, L-arabinose, ribose, D-xylitol, L- ☐xylitol, D-turanose, L-turanose, D-lyxose, D-tagatose, 5-ketogluconic acid.

Does not decompose glycelol, erythritol, adonitol, β-methyl-D-xylose, galactose, mannose, rhamnose, dulcitol, α-methyl-D-mannose, α-methyl-D-glucose, N-acetyl-glucosamine, amidagline, arbutin, aesuculin, salicin, cellobiose, maltose, milk sugar, melibiose, cane sugar, trehalose, inulin, melezitose, raffinose, glycogen, xylitol, gentiobiose, D-fucose, L-fucose, D-arabitol, L-arabitol, 2-ketogluconic acid.

Enzyme activity

| | |
|---|---|
| β-galactositase | negative |
| arginine dihydrolase | negative |
| lygine decarboxylase | negative |
| urease | negative |
| tryptophan deaminase | negative |
| gelatinase | positive |
| Others | |
| use of citric acid | no |
| production of H2S | no |
| production of indole | negative |
| production of acetoin | positive |
| reduction of nitrate | positive |
| anaerobic growth | slightly observed |
| growth at pH 7 | no |
| growth at pH 5.1 | yes |
| growth at 30° C. | no |

From above mentioned taxonomic features, the taxonomic positioning of this bacteria is referred in Bergey's Manual of Systematic Bacteriology, vol 2 p1104–1139, author: S. H. Sneath, editor: P H. Snerth et al. (publisher Williams & Willkins).

This bacteria is a spore-forming rod-shaped bacterium. Although Gram-negative nature of the bacterium is distinct from Gram-positive nature of known species of the genus Bacillus, it is recognized that it is a strain of the genus Bacillus because it grows aerobically.

Among known species of the genus Bacillus, B. acidocaldarius, B. lichenformis, or B. coagulans are known to be thermophilic and acidophilic. However, this strain should not be B. lichenformis and B. coagulance because B. lichenformis and B. coagulance are catalase-positive and can grow at 40° C. but not at 65° C. Also, it is different from the standard species of B. acidocaldarius because it produces acetoin. Therefore, it is not possible to confirm that whether it is a modified species of B. acidocaldarius or it belongs to a different species; the species of this bacteria can not be specified.

Example 2

5 ml of medium (pH 4.8) containing 1.5% of glucose, 1.5% of gelatin and 0.01 % of yeast extract is poured into 5mi test tube and sterilized for 20 minutes at 120° C. NTAP-1 (the shortened name of Bacillus genus NTAP-1 to discriminate the microorganism of this invention) is inoculated on said medium and cultivated with shaking for 4 days. The culture medium is centrifuged for 20 minutes at 8,000 r.p.m., and the activity of the thermostable collagen-decomposing enzyme in the supernatant is measured. Namely, 0.4 ml of enzyme liquid is mixed to 0.1 ml of 1M sodium acetate buffer (pH 4.5) and the mixture is pre-incubated for 5 minutes at 60° C. Then 3mg of Azocoll (azo dye-linked collagen powder: product of Sigma Co., Ltd.) is suspended, and enzyme reaction is carried out at 60° C. with stirring for 1 hour. After the reaction, the reaction mixture is chilled on ice, and insoluble Azocoll was separated by centrifugation.

During the enzyme reaction, Azocoll is decomposed by the enzyme and the supernatant turns red. By measuring the absorbance at 518 nm of the supernatant, the activity of the thermostable collagen-decomposing enzyme is estimated. The amount of enzyme which makes the absorbance at 518 nm increases 0.001 by 1 minute under said condition is defined as 1 unit (U). The concentration of enzyme activity of the obtained supernatant liquid of the cultivated liquid is 3.1 U/ml.

Example 3

6 litter of same medium to Example 2 is poured into a jar fermentor of 10-liter vessel. After sterilized for 30 minutes at 120° C., 200 ml of the NTAP-1 culture is inoculated on said medium. The cultivation is carried out at 60° C. with 6 liters/min aeration for 4 days. The thermostable collagen-decomposing activity of the culture supernatant is measured. The activity of enzyme of the supernatant liquid is 5.0 U/ml.

The resultant supernatant was used as the starting material, the purification and concentration of thermostable collagen-decomposing enzyme was carried out according to the following process.

Ammonium sulfate is added to the supernatant liquid and the precipitate formed by ammonium sulfate 40% saturation was collected and dissolved in 585 ml of 0.01M acetate buffer (pH 5.0). Phenyl-Sepharose (product of AmeshamPharmacia Biotech.) was added to the solution, stirred and mixed for 1 hour, then the mixture was filtrated and the resin is separated. The enzyme activity absorbed to the resin was eluted by washing the resin with 1:1 mixture of 0.01M acetic acid buffer (pH 5.0) and ethylene glycol, and the active fraction was then dialyzed against 0.01M phosphate buffer (pH 7.0).

Then, the solution was passed through DEAE-Sephadex (AmeshamPharmacia Biotech) column which is previously equilibrated with 0.01M phosphate buffer (pH 7.0). The linear gradient (0–1M) of sodium chloride was used to elute the enzyme activity from the column. The eluate was fractioned into about 90 fractions, and the activity of enzyme of each fractions are measured according to the method described in Example 1.

Then, ammonium sulfate is added to the active fractions (233 ml) to 20% saturation. The enzyme activity is absorbed to a column by pass the enzyme solution through the phenyl-Sepharose (AmeshamPharmacia Biotech) column which is previously equilibrated with 0.01M acetic acid buffer (pH 5.0).

Then, the enzyme activity adsorbed to the column was eluted by washing the column with a linear concentration slope (0–50%) of ethylene glycol in the equilibration buffer. The eluted solution is divided into 90 fractions approximately, and the enzyme activity of each fraction is measured according to the measuring method described in Example 1. From fractions of eluted solution, active fractions (total 48 ml) are collected.

This solution is dialyzed against 0.01M phosphate buffer (pH 7.0), then applied to a column of MONO-Q (AmeshamPharmacia Biotech) which is previously made equilibrated with the same buffer. The activity was eluted by washing the column with a linear gradient (0–1M) of sodium chloride.

Active fractions (10.6 ml) were collected and concentrated to 0.5 ml using Centricon (centrifuge concentrator: Amicon Co., Ltd.: said concentrator has an ultrafiltration membrane made of cellulose derivative at the bottom of the container. When mixed solution composed of enzyme and protein is poured into the container and centrifuged by 6000 r.p.m., protein contained in the solution is remained on the membrane, while water or low molecular weight ion passes through the film and recovered as a filtrated liquid.), and divided by a gel filtrating chromatography method, and 1.2 ml of fraction having higher activity is collected. The activity yield of the dissolved fraction from the cultivated liquid is 1.4%, and the concentration of the activated enzyme is 416 U/ml.

The enzyme solution thus obtained was analyzed by SDS-polyacrylamide gel electrophoresis according to Laemmli procedure (Laemmli, U.K., Nature, 1970, 227, 680–685), and molecular weight of the thermostable collagen-decomposing enzyme is estimated to be approximately 46,000.

Example 4

Experiment to Investigate the Substrate Specificity of the Thermostable Collagen-decomposing Enzyme After 5 mg of Azocoll is suspended in 0.4 ml of 0.01M sodium acetate buffer (pH 4.5), 0.1 ml of enzyme solution, whose enzyme concentration is adjusted properly by dilution, is added and allowed to react for 1 hour at 60° C. with constant shaking. After the reaction, the reaction mixture was chilled on ice for 1 hour and then centrifuged. The absorbance at 518 nm of the supernatant is measured. The reaction mixture prepared by same process except using water instead of enzyme solution was used as a blank solution. The absorbance at 518 nm of the reaction mixture whose added Azocoll was perfectly solubilized is measured. The same experiments are carried out on various enzyme concentrations, and the amount of enzyme which gives approximately 50% degradation (to solubilize approximately 2.5 mg Azocoll) under these condition is determined.

By the same process as mentioned above, 5 mg of collagen, gelatin, casein or cow serum albumin (all are the products Nacalai Tesque, Co.) are respectively suspended (or dissolved) in 0.4 ml of 0.01 M sodium acetate buffering solution (pH 4.5), then 0.1 ml of enzyme solution of previously decided concentration is added and reacted for 1 hour at 60° C. with constant shaking. After the reaction, the reaction mixture was kept at 4° C. for 20 minutes and centrifuged. in cases which use casein or bovine serum albumin, 0.5 ml of 50% trichloroacetic acid is added to the reaction mixture and was kept at 4° C. for 20 minutes then centrifuged. The adsorption at 280 nm of the supernatant was measured. From the adsorption value at 280 nm when each proteins are perfectly solubilized, the decomposing ratio of each proteins are measured. When the decomposing rate of Azocoll is regarded as 100%, the relative solubilizing rate of each proteins are listed in Table 1.

TABLE 1

Relative solubilizing rate of each proteins, when decomposing rate of Azocoll is regarded as 100%

| collagen | +++ |
| gelatin | +++ |

TABLE 1-continued

Relative solubilizing rate of each proteins, when decomposing rate of Azocoll is regarded as 100%

Figure 2:
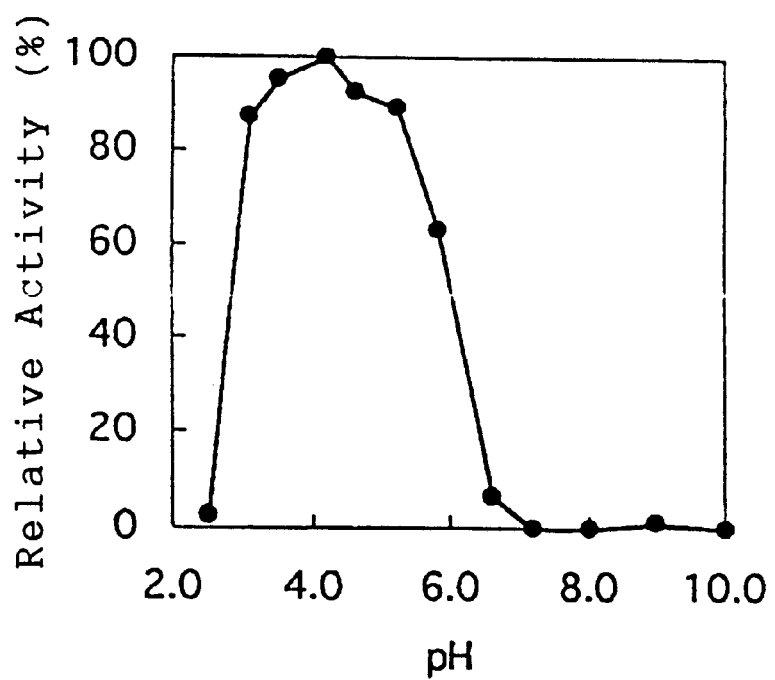
FIG. 2 is the graph showing the relative remaining activity of the thermostable collagen-decomposing enzyme after treatment at various pHs for 1 hour, and in this graph, the activity after treatment at pH 4.1 is taken to be 100%.

| casein | ± |
| albumin | ± |
| keratin | − | remarks
+++: has relative activity greater than 80% to Azocoll
±: has relative activity lower than 20% to Azocoll
−: not reacted The obtained results are shown in FIG. 1. This enzyme is stable up to 60° C. In the meanwhile, the stability of enzymes when enzymes are treated by various pH are investigated. The buffer to be used in specific pH range are listed below.

pH 2.5 to 3.5: 1M glycine-HCl buffer
pH 3.5 to 5.5: 1M sodium acetate buffer
pH 6.0 to 8.0: 1M sodium phosphate buffer
pH 8.0 to 9.0: 1M glycine-NaOH buffer
pH 9.0 to 10.0: 1M sodium phosphate buffer After 0.0025 ml of these buffers and 0.0025 ml of 1% aqueous solution of Tween 80 are added to 0.02 ml of enzyme liquid, placed at the temperature of 60° C. for 1 hour. Then, 0.05 ml of 1M acetic acid buffer (pH 4.0) is added to this treated enzyme liquid and the activity is measured. The obtained result indicates that this enzyme is stable at the pH range from 3 to 6 (FIG. 2).

Example 7

Figure 3:
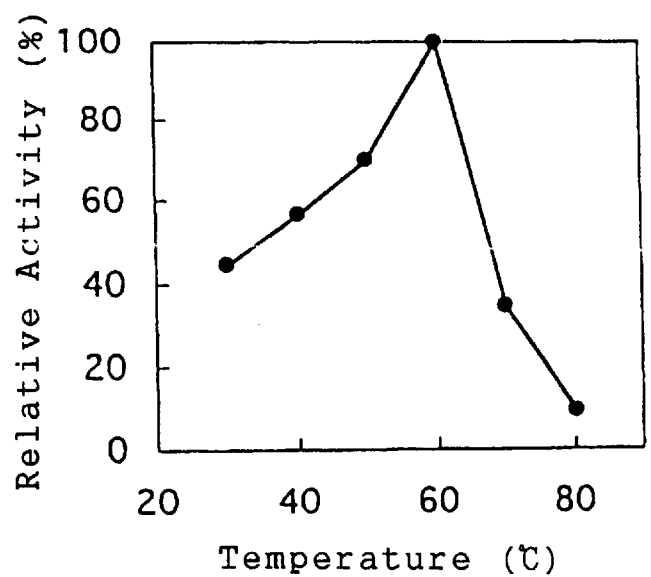
FIG. 3 is the graph showing the relative activity of the thermostable collagen-decomposing enzyme at various temperature, and in this graph, the enzyme activity at 60° C. that indicates maximum activity is taken to be 100%.

Experiment to Investigate the of the Optimum Reaction Temperature and Optimum Reaction pH of Thermostable Collagen-decomposing Enzyme The activity of the thermostable collagen-decomposing enzyme of this invention was measured at 30, 40, 50, 60, 70 and 80° C. The method described in Example 1 was used except changing the reaction temperature. The results showed that this enzyme exhibited the highest activity at 60° C. (refer to FIG. 3).

Figure 4:
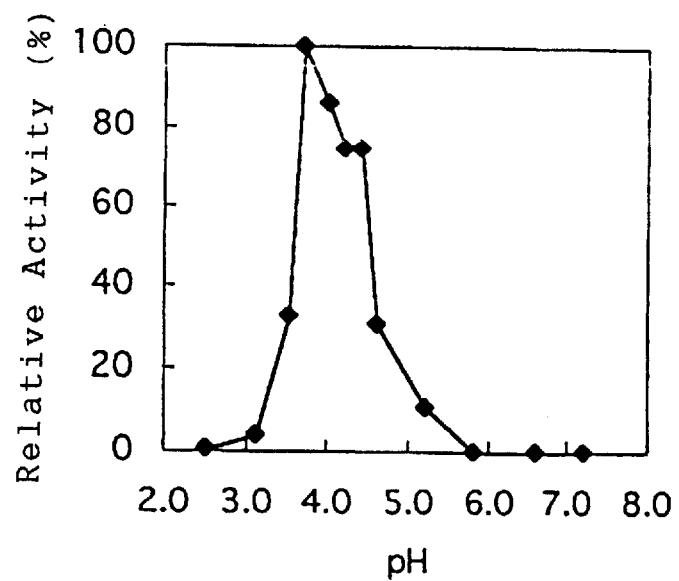
FIG. 4 is the graph showing the relative activity of the thermostable collagen-decomposing enzyme at various pHs, and in this graph, the enzyme activity at pH 3.8 that indicates maximum activity value is taken to be 100%.

Secondly, the activity of this enzyme is measured at various (from pH 2.5 to 7.2). The method for activity measurement was based on the method described in Example 1 except changing buffer component to be used in the reaction system as follows: 0.01M glycine-HCl buffer (pH 2.5 to 7.2), 0.01M sodium acetate buffer (pH 4 to 6) or 0.01M potassium phosphate buffer (pH 6 to 8). The results showed that this enzyme showed the highest activity at pH 3. 7 to 3.9 (refer to FIG. 4).

POTENTIALS FOR THE INDUSTRIAL USE

Obviously from the above mentioned Examples, by the present invention, it becomes possible to prepare effectively a thermostable collagen-decomposing enzyme which is excellent at the optimum temperature, optimum pH and collagen substrate specificity by the use of above mentioned novel microorganism. Therefore, the present invention make it possible to utilize the materials which are not utilized in livestock industries, and largely contribute to the production of collagen peptides that has potential applications in medical, pharmaceutical, and food industries.

What is claimed is:

1. A substantially purified or isolated thermostable collagen-decomposing enzyme obtained from bacillus genus bacteria strain NTAP-1, having a molecular weight of approximately 46,000 Da, an optimum reaction pH between pH 3.5 and 4.5, an optimum reaction temperature between 65° C. and 70° C., wherein the enzyme retains more than 60% of its original activity after heat treatment at 60° C. and pH 6.0 for 4 hours and wherein the enzyme is stable between pH 3 to 6.

2. A method for producing the substantially purified or isolated thermostable collagen-decomposing enzyme described in claim 1 comprising the steps of culturing bacillus genus bacteria strain NTAP-1, deposited under accession number FERM BP-6926, and collecting the resulting thermostable collagen-decomposing enzyme.

3. A substantially purified or isolated microorganism NTAP-1, deposited under accession number FERM BP-6926, which produces the thermostable collagen-decomposing enzyme of claim 1.

4. The substantially purified or isolated thermostable collagen-decomposing enzyme of claim 1, wherein said enzyme decomposes collagen and gelatin at a first decomposing rate greater than 80% relative to that of Azocall, and decomposes casein and albumin at a second decomposing rate lower than 20% relative to that of Azocall.

* * * * *